United States Patent [19]

Lagace et al.

[11] 4,404,119
[45] Sep. 13, 1983

[54] PROCESS FOR RECOVERY OF COBALT OXO CATALYSTS

[75] Inventors: Linda S. Lagace; David A. Young, both of Baton Rouge, La.

[73] Assignee: Exxon Research & Engineering Co., Florham Park, N.J.

[21] Appl. No.: 333,734

[22] Filed: Dec. 23, 1981

[51] Int. Cl.³ .................. B01J 31/40; B01J 31/20; C07C 27/22; C07C 45/50
[52] U.S. Cl. ................... 252/413; 252/414; 252/428; 252/443; 423/417; 568/451; 568/909
[58] Field of Search .............. 252/416, 414, 413, 419, 252/420, 428, 443; 423/417; 568/451, 456, 909

[56] References Cited

U.S. PATENT DOCUMENTS

| | | | |
|---|---|---|---|
| 2,476,263 | 7/1949 | McKeever | 423/417 |
| 2,751,403 | 12/1952 | Mertzweiller | 260/414 |
| 3,265,468 | 4/1963 | Farkas et al. | 23/203 |
| 3,793,437 | 9/1971 | Takasu et al. | 423/417 |
| 3,941,848 | 7/1973 | Kummer et al. | 260/604 |
| 4,255,279 | 7/1979 | Spohn et al. | 252/413 |

FOREIGN PATENT DOCUMENTS

| | | |
|---|---|---|
| 2451473 | of 1976 | Fed. Rep. of Germany . |
| 48-17594 | 5/1973 | Japan . |
| 702221 | 1/1954 | United Kingdom . |
| 1383658 | 2/1971 | United Kingdom . |
| 1390898 | 8/1971 | United Kingdom . |

OTHER PUBLICATIONS

R. Kummer, et al., "New Hydroformylation Technology with Cobalt Carbonyls" *Homogeneous Catalysis—II*, Advances in Chemistry Series No. 132 (D. Forster et al.), pp. 19-26, (ACS 1973).
R. B. King, *Organometallic Synthesis*, vol. 1, p. 98, (Academic Press, 1965).
69 Chem. Abs. 95964d (1968), citing German Pat. No. 1,272,911.
W. Hieber, W. Hübel, Zeitschr. Electrochem., 57, No. 4, pp. 235-243 (1953).
International Critical Tables, vol. 2, pp. 172-190 (McGraw-Hill, 1927).

*Primary Examiner*—P. E. Konopka
*Attorney, Agent, or Firm*—Jack B. Murray, Jr.

[57] ABSTRACT

According to one embodiment of the improved process of this invention, dicobalt octacarbonyl is produced in an olefinic medium by contacting an aqueous solution of a tetracarbonylcobaltate metal salt with an oxygen-containing gas in the presence of an olefinic extractant for dicobalt octacarbonyl to oxidize the tetracarbonylcobaltate anion to dicobalt octacarbonyl which is efficiently extracted into the olefinic phase, thereby producing an organic phase which can then be recovered and passed to a cobalt-catalyzed olefin hydroformylation reaction zone as source of at least a portion of the catalyst and olefin required in the olefin hydroformylation reaction to form the corresponding aldehydes. According to another aspect of this invention, an aqueous solution of tetracarbonylcobaltate metal salt is contacted with an oxygen-containing gas in the presence of gaseous carbon monoxide, and optionally also in the presence of an organic solvent for the dicobalt octacarbonyl, to efficiently oxidize the tetracarbonylcobaltate anion to dicobalt octacarbonyl.

23 Claims, 2 Drawing Figures

PROCESS FOR RECOVERY OF COBALT OXO CATALYSTS

BACKGROUND OF THE INVENTION

1. Field of the Invention

This invention in general relates to a process for recovering cobalt catalysts, and more specifically to an improved process for recovering and recycling cobalt oxo catalysts.

2. Description of the Prior Art

In the well known oxo process, olefins are hydroformylated by reaction with carbon monoxide and hydrogen, generally charged as syn gas mixtures, in the presence of a cobalt oxo catalyst in dissolved form to form a mixture of oxo aldehydes and alcohols. This oxo reaction is typically carried out at syn gas pressures of from about 1500 to 4500 psig and at temperatures of from about 65° to 230° C. Thereafter, the product mixture containing the alcohols and aldehydes is recovered and can then be treated by known means to hydrogenate the aldehydes to form additional quantities of the corresponding alcohols. These alcohols, in turn, are widely used as chemical intermediates in the manufacture of plasticizers, detergents, solvents and the like.

Prior to the hydrogenation step, the crude oxo reaction effluent, which contains dissolved cobalt catalysts, the aldehyde and alcohol products and reaction by-products together with any metallic contaminants, is generally treated to remove the dissolved cobalt catalyst, which then for reasons of economy must be recycled to the oxo reactor.

A wide variety of catalyst recovery/recycle processes have therefore been developed. U.S. Pat. No. 2,751,403 is directed to a process in which cobalt is removed from crude oxo products by extraction with an aqueous acid such as acetic acid to form an aqueous extract containing cobalt in both the cationic and anionic forms, viz., as the anion $[Co(CO)_4]^-$ and the corresponding cobalt salt, cobaltous bis-tetracarbonylcobaltate, $Co^{++}[Co(CO)_4^-]_2$. The aqueous extract is then subjected to oxidation with air or $O_2$ at 38° to 66° C. and at a pH of 5–6 with the addition of a higher molecular weight carboxylic acid salt, e.g., sodium oleate, to convert anionic cobalt to the $Co^{++}$ form and to achieve substantially quantitative recovery of the cobalt as a cobalt soap, e.g., cobaltous oleate, which was the desired catalytic species. The cobalt soap is then extracted into an organic liquid for recycle to the oxo reactor.

However, there has been continuous interest in other, lower cost alternatives to such expensive cobalt soaps, which during use are converted to other forms and have to be reconverted to the soap during the recycle process.

Another form of cobalt useful as oxo catalyst is dicobalt octacarbonyl, $Co_2(CO)_8$.

U.S. Pat. No. 3,265,468 discloses a process for producing $Co_2(CO)_8$ from an aqueous solution of an alkali metal carbonyl of cobalt (e.g., $NaCo(CO)_4$) by acidifying the solution with a mineral acid, followed by extraction, e.g., with toluene, to form an organic phase containing $Co_2(CO)_8$.

In U.S. Pat. No. 3,793,437, crude oxo effluent containing cobalt is contacted with an aqueous solution of metallic extracting agents, such as various metal salts and certain zeolites, in the presence of $H_2$ and CO to form an aqueous salt of carbonyl cobaltate which is subsequently decomposed with an organic acid or a mineral acid to a water-soluble cobalt hydridocarbonyl. The aqueous solution containing the cobalt hydridocarbonyl is then heated in the presence of CO and a water-immiscible organic solvent to form dicobalt octacarbonyl which is extracted into the organic solvent. After further treatment (e.g., drying, dilution or concentration), the organic solvent can be recycled to the oxo reactor. The patentees indicate that the thus-recovered cobalt carbonyl is sensitive to oxygen or oxidizing agents and must be protected from such oxidants as by degassing or by replacement of the ambient atmosphere with inert gas.

R. Kummer, et al., "New Hydroformylation Technology with Cobalt Carbonyls," *Homogeneous Catalysis—II*, Advances in Chemistry Series No. 132 (D. Forster et al.), pp. 19–26 (A.C.S. 1973) relates to a BASF process in which crude oxo product is demetalled at 120° C. and 10 atm. with air and an aqueous formic acid/cobaltous formate solution, and the resulting aqueous $Co^{++}$ formate solution is reacted with CO and $H_2$ to perform anionic cobalt, $Co(CO)_4^-$, in the solution, which is then subjected to an olefin extraction to give an olefin phase containing cobalt as either $Co_2(CO)_8$ or (at low CO pressure) $Co_4(CO)_{12}$. Kummer et al. describes the crude oxo product demetalling step by the following equation (I):

$$Co_2(CO)_8 + O_2 + 4H_3O^+ + 4HCOO^- \longrightarrow$$
$$2Co^{++} + 4HCOO^- + 6H_2O + 8CO \qquad (I)$$

The authors point out that the resulting aqueous phase contains all the cobalt and that only water-soluble $Co^{++}$ compounds are formed.

German Pat. No. 1,272,911 to BASF, as cited at 69 Chem. Abs. 95964d (1968), describes the demetalling of a crude oxo product at 116° C. and 30 atm. with air, acetic acid, water and a recycled $Co^{++}$ salt solution, using a residence time in the demetalling zone of 3 seconds, to give an organic phase containing practically no cobalt.

The following BASF patents relate to similar processes: U.S. Pat. No. 3,941,848; British Pat. Nos. 1,383,658 and 1,390,898; and German Offenlegungschrift No. 2,451,473 (1976).

U.S. Pat. No. 4,255,279 contacts a crude oxo effluent in a first step with an aqueous $Co^{++}$ salt of an organic or inorganic acid to extract cobalt into the aqueous phase. After separation from the thus-treated crude oxo product, the aqueous phase, which contains cationic and anionic cobalt, $Co^{++}$ and $Co(CO)_4^-$, is treated with syn gas to perform additional $Co^{++}$ into the anionic, $Co(CO)_4^-$, form. The preformed effluent is then contacted with an organic solvent to extract cobalt carbonyls therefrom into the organic phase for ultimate recycle to the oxo reactor. The treated crude oxo product obtained from the first step still contains some cobalt in an oil-soluble form, e.g., dicobalt octacarbonyl, and is further demetalled by treatment at 65° to 93° C. with an aqueous organic or inorganic acid and oxygen to oxidize the cobalt to a water-soluble form, e.g., $Co^{++}$ salt of the selected acid. The patentees indicate that substantially all of the cobalt is thereby separated from the organic layer, resulting in an oxo product containing cobalt in a concentration of about 10 ppm or less.

Japanese Patent Publication No. 73/17,594 (May 30, 1973) oxidizes a cobalt hydrocarbonyl water-soluble metal salt (e.g., $NaCo(CO)_4$ or $Co[Co(CO)_4]_2$) in aqueous solution with air or $O_2$ to form dicobalt octacarbonyl solids, followed by extraction thereof using an organic solvent or raw material olefin or their mixture. Alternatively, the patentees indicate that the organic solvent can be added in the oxidation step to extract the dicobalt octacarbonyl directly into the organic solvent layer.

In R. B. King, *Organometallic Synthesis*, vol. 1, p. 98 (Academic Press 1965), it is indicated that $Co_2(CO)_8$ crystals are soluble in organic solvents; are unstable to both thermal decomposition and air oxidation; and rapidly lose CO at 50° C. to form $Co_4(CO)_{12}$ and ultimately cobalt metal. On exposure to air for several minutes, $Co_2(CO)_8$ crystals are said to be oxidized to a $Co^{++}$ derivative, which is presumed to be either the oxide or the carbonate. Also, $Co_2(CO)_8$ crystals, when isolated by crystallization from organic solvents, are said to be pyrophoric if obtained as finely divided crystals. A preparatory procedure is therefore suggested in which cobalt (II) acetate tetrahydrate is reacted at 160°–180° C. with CO and $H_2$ to form acetic acid and $Co_2(CO)_8$ crystals, which are isolated by filtration under $N_2$.

W. Hieber and W. Hübel, *Zeitschr. Elektrochem.* 57, no. 4; pp 235–243 (1953) indicate that solutions of cobalt carbonyl hydride are very sensitive to oxidizing agents and that dimeric cobalt carbonyl flakes are immediately formed from even minute traces of atmospheric oxygen (see Section I, paragraph 2).

SUMMARY OF THE INVENTION

According to one embodiment of the improved process of this invention, dicobalt octacarbonyl is produced in an olefinic medium by contacting an aqueous solution of a tetracarbonylcobaltate metal salt with an oxygen-containing gas in the presence of an olefinic extractant for dicobalt octacarbonyl to oxidize the tetracarbonyl-cobaltate anion to dicobalt octacarbonyl which is efficiently extracted into the olefinic phase, thereby producing an organic phase which can then be recovered and passed to a cobalt-catalyzed olefin hydroformylation reaction zone as source of at least a portion of the catalyst and olefin required in the olefin hydroformylation reaction to form the corresponding aldehydes. It has been surprisingly found, contrary to the teachings of the prior art, that olefins can be employed as the extractant liquid in the oxidation zone without formation of economically disadvantageous olefin-oxidation by-products.

According to another aspect of the process of this invention, it has been found that greatly improved yields of dicobalt octacarbonyl can be obtained by contacting an aqueous solution of tetracarbonylcobaltate metal salt with an oxygen-containing gas in the presence of gaseous carbon monoxide, and optionally also in the presence of an organic solvent for the dicobalt octacarbonyl, to efficiently oxidize the tetracarbonylcobaltate anion to dicobalt octacarbonyl. If the oxidation is effected in an aqueous medium, the resulting aqueous slurry of dicobalt octacarbonyl can be contacted with an organic solvent to form an organic phase containing dicobalt octacarbonyl suitable for recycle to hydroformylation. Alternatively, if the oxidation is effected in the presence of an organic solvent, an organic phase containing dicobalt octacarbonyl can be recovered from the oxidation reaction zone for recycle to the hydroformylation reaction.

According to a further embodiment of the improved process of this invention, crude oxo products produced by the cobalt-catalyzed hydroformylation of olefins and containing dissolved cobalt catalyst together with hydroformylation products are contacted in a low pressure extraction zone with an aqueous solution of a $Co^{++}$ salt of an organic or inorganic acid to form an aqueous phase containing water-soluble cobalt values, i.e., $Co^{++}$ $[Co(CO)_4^-]_2$ and $Co^{++}$ salts of said acid, and a treated oxo product depleted in dissolved cobalt values. The aqueous phase thus obtained is then contacted with $H_2$ and CO gas at elevated temperatures and pressures in a preforming zone to form an aqueous solution containing additional amounts of $Co^{++}[Co(CO)_4^-]_2$ from said $Co^{++}$ acid-salt. Thereafter, the aqueous solution is contacted with an $O_2$-containing gas to form dicobalt octacarbonyl from the cobalt values dissolved therein. The oxidized aqueous product is then contacted in a separate extraction zone with an organic extractant for said dicobalt octacarbonyl to provide an organic phase containing dicobalt octacarbonyl suitable for recycle to said hydroformylation.

According to another and preferred embodiment, the aqueous solution of $Co^{++}[Co(CO)_4^-]_2$ withdrawn from the performing zone is contacted with the $O_2$-containing gas in the oxidation zone at elevated pressures and in the presence of the organic solvent for the dicobalt octacarbonyl to form an organic phase containing dicobalt octacarbonyl oxidation product suitable for recycle to the hydroformylation as catalyst.

DETAILED DESCRIPTION OF THE INVENTION

According to one embodiment of this invention, an aqueous solution of a tetracarbonylcobaltate salt is contacted with an $O_2$-containing gas in a reaction zone in the presence of a free organic or inorganic, water-soluble acid and in the presence of an olefinic liquid extractant for $Co_2(CO)_8$ to form an olefinic phase containing dicobalt octacarbonyl and substantially free of oxidation by-products of the olefinic extractant, and an aqueous phase substantially free of $Co_2(CO)_8$.

The tetracarbonylcobaltate salt in the aqueous phase can be represented in its dissociated form as $M^{+n}[Co(CO)_4^-]_n$, wherein "M" is a cation and "n" is an integer corresponding to the valence of "M". Thus, "M" can comprise a member selected from the group consisting of Co, alkali and alkaline earth metal, Fe, Cu, Mo, Ni, Al, $NH_4^+$, Zn, $PR_4^+$, $NR_4^+$, $HNR_3^+$, $H_2NR_2^+$, and $H_3NR^+$, wherein "R" is alkyl of 1 to 20 carbon atoms, aryl of 6 to 18 carbon atoms, alkaryl and aralkyl of 7 to 18 carbon atoms and heterocyclic derivatives of the foregoing aromatic groups. Exemplary tetracarbonyl-cobaltate metal salts, therefore, are $NaCo(CO)_4$, $Co[Co(CO)_4]_2$, $KCo(CO)_4$, $Mg[Co(CO)_4]_2$, $Al[Co(CO)_4]_3$, $Cu[Co(CO)_4]_2$, and the like of which $Co[Co(CO)_4]_2$ is especially preferred.

While we do not wish to be bound by any theory, it is believed the reaction forming $Co_2(CO)_8$ in the oxidation zone can be illustrated by the following expression in which acetic acid is employed as an illustrative acid and cobaltous tetracarbonylcobaltate is the illustrative reactant salt:

$$Co[Co(CO)_4]_2 + 2HOAc + \tfrac{1}{2}O_2 \rightarrow Co_2(CO)_8 + Co(OAc)_2 + H_2O \qquad (II)$$

Suitable organic or inorganic acids will be water soluble in an amount of at least about 0.04 gram per gram of water at 25° C. Illustrative of suitable organic or inorganic acids are monocarboxylic acids having from 1 to 4 carbon atoms per molecule (which are preferred), dicarboxylic acids having from 2 to 5 carbon atoms per molecule, and the like. Exemplary of such acids, therefore, are alkanoic acids such as formic, acetic, propionic, butyric, isobutyric, propionic, oxalic, malonic, succinic, and the like. The quantity of acid charged to the oxidation zone can vary but is preferably from about 1 to 50, and more preferably 2 to 25, times the moles stoichiometrically required to react with the quantity of the bis-tetracarbonylcobaltate metal salt introduced to the oxidation zone.

The aqueous feed to the oxidation zone will generally contain the tetracarbonylcobaltate metal salt in a concentration of from about 0.5 to 25 wt. %, preferably from about 1 to 10 wt. %, calculated as $Co(CO)_4^-$, and the selected inorganic or organic acid in a concentration of from about 0.2 to 10 wt. %. However, these concentration ranges are not critical and can vary widely.

The olefin fed to the oxidation zone can comprise any carbon compound containing olefinic linkages. Amenable to the reaction are long and short chained olefinic compounds, depending upon the type aldehydes desired. Not only olefins, but most organic compounds possessing at least one non-aromatic carbon-carbon double bond may be reacted by this method. Thus, straight and branch-chained olefins and diolefins such as propylene, butylene, pentene, hexene, heptene, butadiene, pentadiene, styrene, olefin polymers such as di- and tri-isobutylene and hexene and heptene dimers, polypropylene, olefinic fractions from the hydrocarbon synthesis process, steam cracking or catalytic cracking operations, and other sources of hydrocarbon fractions containing olefins may be used as starting material, depending upon the nature of the final product desired. Also suitable are olefins bearing functional groups such as —C≡N, —OH, —halide and the like which do not adversely affect the hydroformylation reaction. Illustrative of such functionally substituted olefins are acrylonitrile, alkyl alcohol, alkenyl esters of acrylic acid, acrylic acid, vinyl halides and the like. Preferred are olefins having from 4 to 20 carbon atoms, more preferably from 6 to 12 carbon atons, (such as butenes, pentenes, hexenes, heptenes, octenes, decenes, dodecenes and the like), and aryl-substituted alpha-olefins (such as styrene, stilbene, divinylbenzenes and the like).

The selected liquid olefinic extractant preferably corresponds to the olefin to be hydroformylated in the subsequent hydroformylation reaction, and is preferably used in an amount of from about 0.1 to 10 volumes for volume of aqueous feed introduced to the oxidation zone.

The aqueous feed to the oxidation zone can also contain water-soluble metal salts of any of the above inorganic or organic acids, in which the salt's cation can comprise any of the above "M" cations and preferably corresponds to the metal cation associated with the tetracarbonylcobaltate metal salt. The concentration of these inorganic or organic metal salts is not critical and will vary depending on the precise metal cation, the acid anion, and other factors. For example, $Co^{++}$ salts of such organic and inorganic acids, when present, will generally be in a concentration of from about 0.5 to 4.0 wt. %, calculated as elemental cobalt, based on the amount of water in the oxidation zone.

The source of the aqueous solution containing the tetracarbonylcobaltate metal salt and free acid is not critical. A preferred aqueous stream for oxidation in accordance with this invention is the aqueous effluent from a low pressure extraction of crude olefin-hydroformylation reaction products, as will be described in more detail below. The oxidation reaction can be performed in a continuous, semi-continuous or batchwise manner, with the components being introduced thereto separately or in any admixture. The temperature employed in the oxidation zone can range from about 0° to 90° C., and preferably from about 10° to 50° C. Pressures are not critical and can vary from about 15 to 1500 psig, more preferably from about 50 to 500 psig. However, pressures outside this range are also suitable. The molecule oxygen can be introduced in any convenient form, such as a gaseous feed of pure oxygen or as oxygen admixed with inert gases such as nitrogen, argon and the like. Atmospheric air is entirely suitable for this oxidation. The residence time of the aqueous mixture in the oxidation zone can also vary widely, and will generally range from about 5 seconds to 1 hour, and preferably from about 0.5 to 15 minutes.

The effluent from the oxidation zone comprises organic and aqueous phases which can be separated and recovered using conventional equipment and techniques. The aqueous phase is depleted in carbonylcobaltate values and is substantially free of $Co_2(CO)_8$. The olefinic phase, which will typically contain from about 0.1 to 11 wt. %, preferably from about 0.5 to 6 wt.%, dissolved $Co_2(CO)_8$, has been found to be substantially free of oxidation by-products formed by reaction of the olefin extractant and $O_2$ in the oxidation zone. The recovered olefinic phase is therefore suitable as feed to a cobalt-catalyzed olefin hydroformylation reaction to supply at least a portion of the homogeneous cobalt catalyst required therein.

Figure 1:
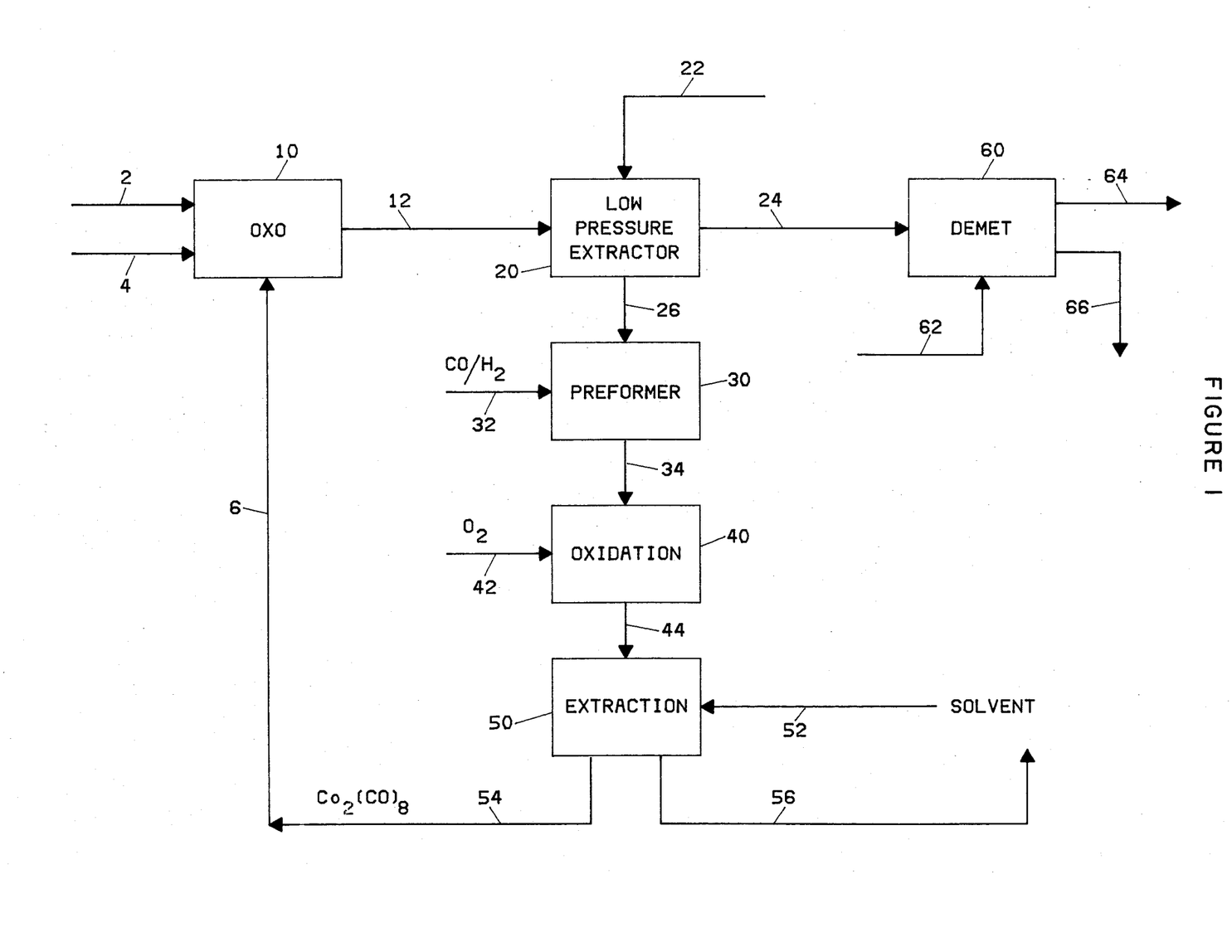
FIG. 1 is a diagrammatic illustration of one embodiment of the process of this invention.

Reference is now made to the accompanying drawings, wherein like numerals refer to the same or similar elements. Referring first to FIG. 1, an olefin feed is introduced via conduit 2 to oxo reactor 10 to which is also fed a mixture of CO and $H_2$ (synthesis gas) via conduit 4 and an organic liquid containing dissolved cobalt catalyst via conduit 6. The oxo reaction is conventional and typically employs a temperature of from about 65° to 240° C. and syn gas pressures of from about 1500 to 4500 psig.

The olefin fed to the oxo reactor 10 can comprise any carbon compound containing olefinic linkages described above as useful in the oxidation zone to extract the $Co_2(CO)_8$. Thus, straight and branch-chained olefins and diolefins such as propylene, butylene, pentene, hexene, heptene, butadiene, pentadiene, styrene, olefin polymers such as di- and tri-isobutylene and hexene and heptene dimers, polypropylene, olefinic fractions from the hydrocarbon synthesis process, steam cracking or catalytic cracking operations, and other sources of hydrocarbon fractions containing olefins may be used as starting material, depending upon the nature of the final product desired. Also suitable are olefins bearing functional groups such as —C≡N, —OH, —halide and the like which do not adversely affect the hydroformylation reaction. Illustrative of such functionally substituted olefins are acrylonitrile, allyl alcohol, alkenyl esters of acrylic acid, acrylic acid, vinyl halides and the like. Preferred are olefins having from 2 to 20 carbon atoms (such as ethylene, propylene, butenes, pentenes, hexenes, heptenes, octenes, decenes, dodecenes and the like) and aryl-substituted alpha-olefins (such as styrene, stilbene, divinylbenzenes and the like).

Crude oxo product is withdrawn from oxo reactor 10 via conduit 12 and comprises dissolved cobalt catalyst, unreacted olefin, hydroformylation product and hydroformylation by-products. The dissolved catalyst species in the oxo reactor, and hence in the crude oxo products is considered to be hydrido cobalt tetracarbonyl, $HCo(CO)_4$, which is in equilibrium with hydrido cobalt tricarbonyl, $HCo(CO)_3$, according to "Organic Synthesis via Metal Carbonyls," Wender and Pino, Inter Science Publishers, volume I, pages 249-251. The crude oxo product will generally contain cobalt in an amount of from about 0.05 to 3.0 wt. %, calculated as elemental cobalt. The concentration of aldehyde in the crude oxo product is not critical but will generally vary from about 40 to 75 wt. %.

The crude oxo product is introduced via conduit 12 into first extraction zone 20 wherein the crude oxo product is contacted with an aqueous solution containing a $Co^{++}$ salt of an organic or inorganic acid to form a treated oxo product depleted in dissolved cobalt values and an aqueous phase containing $Co^{++}[Co(CO)_4^-]_2$ together with an excess $Co^{++}$ salt of said acid. While the conditions employed in this first extraction zone 20 can vary widely, the extraction will generally be performed at a temperature within the range of from about 10° to 95° C., and preferably from 50° to 90° C., and at a pressure of from about atmospheric to about 200 psig, preferably from about 20 to 100 psig. The organic or inorganic acid which forms the anion of the $Co^{++}$ salt introduced via conduit 22 can comprise any organic or inorganic acid the cobalt salt of which is water soluble in an amount of at least about 0.04 gram per gram of water at 25° C. Illustrative of suitable organic or inorganic acids are monocarboxylic acids having from 1 to 4 carbon atoms per molecule, dicarboxylic acid having from 2 to 5 carbon atoms per molecule, and the like. Thus, illustrative of suitable cobalt salt are cobaltous acetate, formate, propionate, butyrate and isobutyrate, and cobaltous oxalate, malonate, succinate and glutarate and mixtures of the above. The concentration of the $Co^{++}$ salt of said organic or inorganic acid in the aqueous medium introduced via conduit 22 is not critical but will generally range from about 0.5 to 4.0 wt. %, calculated as elemental cobalt. The quantity of said aqueous extractant which is introduced via conduit 22 can also vary widely, and the aqueous extractant will generally be used in an amount of from about 0.005 to 0.5, and preferably from about 0.02 to 0.16 volume of said aqueous extractant per volume of crude oxo product introduced via conduit 12.

Preferably, the crude oxo product is extracted in zone 20 in the presence of an inert gas such as nitrogen or synthesis gas (i.e., any mixture of CO and $H_2$). When the extraction in low pressure extractor 20 is performed in the presence of synthesis gas, the synthesis gas preferably has a composition of from about 40 to 60 vol % CO and from about 40 to 60 vol % $H_2$.

The extraction of the crude oxo product in zone 20 is preferably conducted for a time sufficient to extract a major amount, i.e., more than ½, and preferably at least about 90%, of the cobalt values dissolved in the crude oxo product, calculated as elemental cobalt.

Following the treatment in extraction zone 20, the aqueous and organic phases thus obtained are separated as by settling employing conventional equipment. The organic phase comprises the treated oxo product depleted in dissolved cobalt values and now contains, e.g., up to about ⅛ of the original amount of cobalt. This treated oxo product can be passed via conduit 24 into demetalling zone 60 wherein it is contacted at a temperature of from 35° to 95° C. with oxygen or air, acetic acid or other suitable acid and water which is introduced thereto via conduit 62, thereby converting the remaining cobalt values into the aqueous soluble cobaltous salt of the acid, e.g., cobaltous acetate. The organic and inorganic acid suitable for use in demetalling zone 60 can comprise any of the organic or inorganic acids which are useful (as described above) in the aqueous extractants introduced to zone 20 via conduit 22.

From demetalling zone 60 there are withdrawn organic and aqueous phases, obtained as by settling, employing conventional equipment. The organic phase which is withdrawn via conduit 64 comprises the oxo product substantially free of dissolved cobalt values and generally less than about 10 ppm Co. The aqueous phase withdrawn from demetalling zone 60 via conduit 66 comprises an aqueous mixture containing the dissolved cobaltous salt and can be passed (after addition of make-up cobaltous acid salt, if needed) to conduit 22 as the aqueous extractant medium fed to first extraction zone 20. The make-up cobalt may be needed because some thermal degradation of the hydrido cobalt tetracarbonyl may occur in the process since it does not operate at 100% efficiency. Depending on operating conditions in oxo reactor 10, the amount of make-up that must be added from an outside source typically ranges from 0 to 10 wt.% of the total cobalt employed. The addition of the water-soluble cobaltous acid salt is a simple and convenient way of accomplishing the required make-up of cobalt values.

The aqueous phase withdrawn from low pressure extraction zone 20 via conduit 26 comprises an aqueous solution containing $Co[Co(CO)_4]_2$, and any excess cobaltous salt of the selected acid, e.g., cobalt acetate, in addition to free acid, e.g., acetic acid. This solution is introduced via conduit 26 into preforming zone 30 to which synthesis gas is supplied via conduit 32. (The synthesis gas composition is not critical but will generally contain from about 40 to 60 vol. % CO and from about 60 to 40 vol. % $H_2$.) In zone 30, the aqueous solution is treated at a temperature of from about 0° to 200° C. and at a synthesis gas pressure of from 1500 to 4500 psig. Additional quantities of $Co[Co(CO)_4]_2$ and free acid are formed therein from the excess cobaltous acid salt introduced thereto via conduit 26. While again we do not wish to be bound by any theory, it is believed the preforming reaction can be illustrated by the following equation (III):

$$3Co(OAc)_2 + 3H_2 + 8CO \xrightarrow{Co[Co(CO)_4]_2} Co[Co(CO)_4]_2 + 6 HCAc \quad (III)$$

The $Co[Co(CO)_4]_2$ in the aqueous feed to preformer 30 acts as a homogeneous catalyst for the conversion of the cobaltous salt. A maximum of about 67% of the total cobalt in the solution can exist in the carbonyl form at the conclusion of the preforming step, as shown by Equation I.

The preformer 30 can also employ a heterogeneous catalyst such as activated charcoal, zeolites, basic ion exchange resins, or the like. Suitable types of activated carbon are for example peat carbon, animal charcoal or charcoal derived from sugar. Preferred basic ion exchange resins are those which contain primary, secondary or tertiary amino groups. Ion exchange resins based on polystyrene which contain tertiary amino groups or quaternary amino groups in the basic form are especially suitable, exemplary of which are Amberlite IR45 and Dowex 4. Also suitable are macroreticular types such as Amberlyst A 21, Lewatit MP 62, Lewatit MP 64, Imac A 20, Cerolit G, Amberlite IRA 93, and Amberlist A 26. The activated carbon, zeolite or basic ion exchange resin is preferably loaded with cobalt carbonyl until it is saturated. This is generally achieved by passing aqueous solutions of cobalt salts together with the said gas mixture of carbon monoxide and hydrogen over the activated carbon, zeolite, or basic ion exchange resin under the specified reaction conditions until they are saturated, that is until cobalt carbonyl or cobalt carbonyl hydride is detected analytically in the discharge.

The low pressure extraction in zone 20, the preforming step and the demetalling oxidation of zone 60 are more completely described in U.S. Pat. No. 4,255,279, which is hereby incorporated by reference.

A treated aqueous phase is withdrawn from preforming zone 30 via conduit 34 and passed to oxidation zone 40 wherein the aqueous phase is contacted in the presence of free organic or inorganic acid with molecular oxygen introduced thereto via conduit 42 in order to form dicobalt octacarbonyl therein. Any of the above-described acids whose cobaltous salts are useful in the aqueous extractant fed via conduit 22 to low pressure extractor 20 are also suitable for use in the oxidation zone. Typically, the acid will correspond to the cobaltous acid salt used in the first extraction step 20. Exemplary of such acids, therefore, are alkanoic acids such as formic, acetic, propionic, butyric, isobutyric, propionic and the like. The quantity of acid charged to the oxidation zone can vary but is preferably from about 1 to 50, and more preferably 2 to 25, times the moles stoichiometrically required to react with the quantity of cobaltous bis-tetracarbonylcobaltate introduced to the oxidation zone via conduit 34.

The aqueous phase introduced via conduit 34 will generally contain from about 0.5 to 25, preferably from 1 to 10, wt. % cobaltous bis-tetracarbonylcobaltate, calculated as elemental cobalt, and can also contain cobaltous salts of the inorganic or organic acid selected for use in first extraction zone 20. When present, such cobaltous inorganic and organic acid salts will be present in an amount generally from about 0.2 to 10 wt. %, preferably from about 1 to 3 wt. %, in the case of cobaltous alkanoates (e.g., acetate).

The oxygen-containing gas can be contacted with the aqueous phase in zone 40 in any convenient manner, such as by gas sparging, or by use of suitable agitation devise to accelerate absorption of the oxygen into the liquid phase for reaction, or a combination thereof.

The temperature employed in zone 40 can range from about 0° to 90° C., and preferably from about 10° to 50° C. Pressures in zone 40 are not critical and can vary from about 15 to 1500 psig, more preferably from about 50 to 500 psig. However, pressures outside this range are also suitable. The molecular oxygen can be introduced in any convenient form, such as a gaseous feed of pure oxygen or as oxygen admixed with inert gases such as nitrogen, argon and the like. Atmospheric air is entirely suitable for this oxidation. The residence time of the aqueous mixture in oxidation zone 40 can also vary widely, and will generally range from about 5 seconds to 1 hour, and preferably from about 0.5 to 15 minutes.

The effluent from oxidation zone 40 comprises an aqueous slurry of solid dicobalt octacarbonyl and contains dissolved cobaltous acid salt, generally in an amount of from about 0.5 to 5.0 wt. % solid $Co_2(CO)_8$ and from about 0.2 to 10.0 wt. % dissolved cobaltous acid salt, based on the weight of the total aqueous slurry. This slurry is then passed via conduit 44 from oxidation zone 40 to second extraction zone 50 wherein an extraction is performed in the presence of an organic solvent for the dicobalt octacarbonyl, introduced thereto via conduit 52. The organic extracting liquid can be an olefinic or non-olefinic liquid and may be selected from U.O.P. olefins (defined in U.S. Pat. No. 4,078,132), the feed olefins (e.g., a portion such as 10% of the olefin feed to reactor 10), hydroformylation product from any stage, the heavy oxygenated fraction (HOF) bottoms from the distillation of demetalled oxo alcohol product, or other suitable solvents alone or in combination. Other illustrative suitable organic solvents are those which are inert to the dicobalt octacarbonyl and which do not interfere with the desired hydroformylation reaction on recycle to oxo reactor 10, including for example saturated hydrocarbons, aromatic hydrocarbons, acetals, ethers, esters and mixtures comprising two or more of these solvents. Saturated hydrocarbons include, for example, methane, ethane, propane, butane, pentane, hexane, heptane, octane, nonane, decane, gasoline, cyclopentane, cyclohexane and decaline; aromatic hydrocarbons include, for example, benzene, toluene, xylene, tetraline, naphthalene and methylnaphthalene; acetals include, for example, reaction products between the aldehydes and alcohols formed in the hydroformylation such as the bis-butylacetal of butyraldehyde, bis-decylacetal of decanal and the like; ethers include, for example, diethyl ether, di-i-propylether, d-n-butylether, di-i-butylether, ethylene glycol dimethyl ether and ethylene glycol diethyl ether, and esters include, for example, methyl acetate, ethyl formate, propyl acetate and butyl acetate.

The conditions employed in second extraction zone 50 can vary widely. The temperature of extraction will generally range from about 0° to 90° C., preferably from about 10° to 50° C., the pressure will generally range up to about 4500 psig, preferably from about 1 to 1000 psig, more preferably from about 15 to 300 psig, and the quantity of organic solvent employed will generally range from about 0.1 to 10 volumes of the organic solvent per volume of the aqueous mixture introduced to zone 50 via conduit 44. The extraction in zone 50 can be effected in the presence of mixtures of CO and hydrogen (e.g., syn gas having from 40 to 60% CO and from 60 to 40% $H_2$), and inert gases such as nitrogen, methane (e.g., natural gas) and the like. Preferably, oxygen is excluded from second extraction zone 50 when the temperature of extraction exceeds about 90° C., more preferably exceeds about 50° C.

The aqueous and organic phases are separated using conventional equipment and techniques, and the organic phase, which comprises the organic solvent containing dissolved dicobalt octacarbonyl, can be passed via conduit 54 to conduit 6 as recycle catalyst feed to oxo reactor 10. This recycled organic phase will generally contain from about 0.1 to 11 wt.% dissolved $Co_2(CO)_8$, and preferably from about 3 to 8 wt.% $Co_2(CO)_8$. The organic phase can also contain other Co carbonyls and complexes, such as $Co_4(CO)_{12}$, $\pi$-olefin cobalt tetracarbonyl and tricarbonyl complexes, and alkyl and acyl cobalt tetracarbonyls and tricarbonyls wherein the foregoing olefin, alkyl and acyl groups are derived from the olefin fed to the hydroformylation. The aqueous phase, which will contain the dissolved cobaltous acid salt, can be withdrawn from extraction zone 50 via conduit 56 and can be recycled, if desired, to conduit 22 (together with make-up cobaltous acid salt, if necessary) as a portion or all of the aqueous extractant introduced to zone 20. If desired, the aqueous phase in conduit 56 can also be passed to conduit 26 for formation of additional amounts of $Co[Co(CO)_4]_2$ from the cobalt content thereof, and/or to conduit 62 to aid in the final demetalling step in zone 60.

It will be understood that the aqueous solution containing cobaltous acid salt withdrawn via conduit 56, as well as the aqueous solution withdrawn from demetalling zone 60 via conduit 66, can be passed to a suitable storage vessel (not shown) which can serve as intermediate storage of the aqueous extractant ultimately intended for recycle to conduits 22, 26 or 62 as described above. It should be noted that there is no discarding of the circulating stream, which both conserves cobalt and avoids pollution. However, if excess water accumulates, it can be removed by withdrawing a sidestream (not shown) from such storage vessel, which sidestream can then be treated to evaporate a portion of the water therefrom and to return the thus-concentrated stream to the storage vessel.

Figure 2:
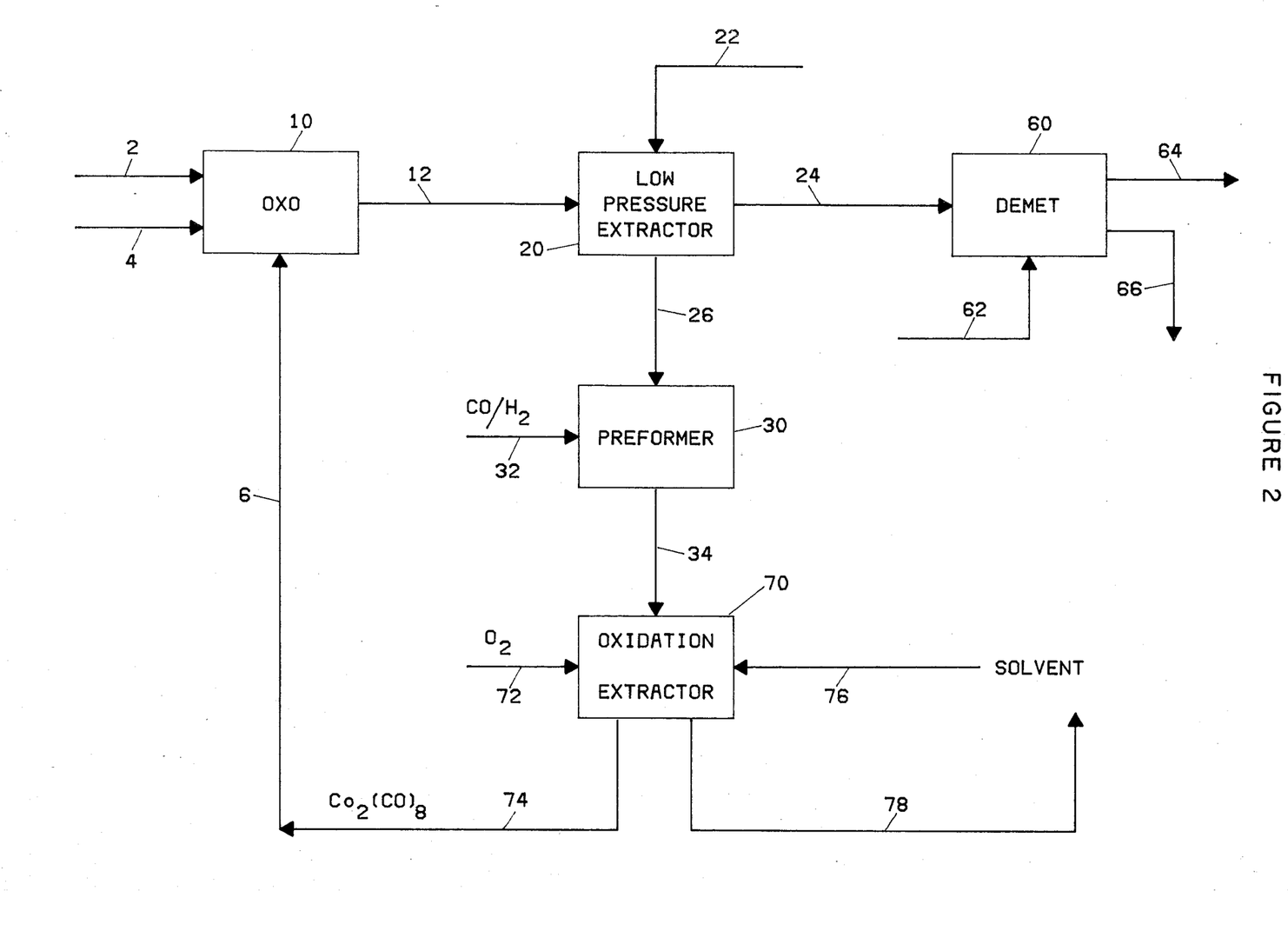
FIG. 2 is a diagrammatic illustration of a second embodiment of the process of this invention.

Referring now to FIG. 2, wherein another embodiment of the process of this invention is illustrated, crude oxo product withdrawn from oxo reactor 10 via conduit 12 is treated as described above in low pressure extraction zone 20 with an aqueous extractant containing the selected cobaltous salt of a suitable organic or inorganic acid. An aqueous phase is formed which is withdrawn via conduit 26 and which contains dissolved $Co[Co(CO)_4]_2$, together with any excess cobaltous salt. This stream is then introduced into preformer 30. In preformer 30, as described above, this aqueous liquid is contacted with synthesis gas to preform additional quantities of the $Co[Co(CO)_4]_2$ from the excess cobaltous salt. The aqueous solution of the water-soluble cobalt carbonyl complex is withdrawn from zone 30 via conduit 34 and is passed to zone 70 wherein the aqueous liquid is contacted with an organic solvent, introduced thereto via conduit 76, and molecular oxygen, introduced thereto via conduit 72, in order to effect simultaneous oxidation of the $Co(CO)_4^-$ to dicobalt octacarbonyl which is then efficiently and simultaneously extracted into the organic solvent phase. The conditions of temperature employed in zone 70 correspond to those useful in oxidation zone 40, as described above. Thus, temperatures of from about 0° to 90° C., and preferably from about 10° to 50° C. are suitable. To effect the most efficient and complete extraction of the thus-formed $Co_2(CO)_8$ into the organic phase, the pressure in zone 70 should range up to about 1500 psig, preferably from about 15 to 1000 psig. As in oxidation zone 40 of FIG. 1, the residence time of the liquids passed to zone 70 can vary widely, but will generally range from about 5 seconds to 1 hour, and preferably from about 0.5 to 15 minutes.

The type and quantities of organic solvents useful in zone 70 in this embodiment correspond to the solvents and amounts described above as suitable for use in extractor 50.

The organic and aqueous phases formed in zone 70 are then separated and the organic phase withdrawn via conduit 74. The withdrawn organic phase contains dissolved dicobalt octacarbonyl and can be passed to conduit 6 for recycle to oxo reactor 10. The aqueous phase, containing dissolved cobaltous acid salt, as above described, can be withdrawn from zone 70 via conduit 78 and, as before, recycled to conduits 22, 26 or 62 or to intermediate storage for ultimate recycle thereto.

It has been surprisingly found that the yields of $Co_2(CO)_8$ in the oxidation zones of this invention (e.g., zones 40 and 70) can be significantly improved in the oxidation of the aqueous $Co(CO)_4^-$ values by charging gaseous carbon monoxide to the oxidation zone.

The gaseous CO can be introduced as CO or as a CO-containing gas, such as syn gas (mixtures of $H_2$ and CO), and can be introduced in any convenient manner, such as with the oxygen-feed or via a separate conduit (not shown). Alternatively, the CO can be introduced via conduit 26 with the aqueous $Co(CO)_4^-$ values, which will then comprise a two-phase (gas/liquid) feed to the oxidation zone. The CO partial pressures in the oxidation zone 40 will generally range from about 10 to 4500 psig, and preferably from about 50 to 2000 psig, and the total pressure (sum of CO+$O_2$ partial pressures) will generally range from about 20 to 4500 psig, preferably from about 50 to 2500 psig. Preferably, mixtures of CO and oxygen-containing gas which are outside of the explosive range are employed. Thus, the volume percent CO in the total gas mixture for a CO/air mixture is preferably outside the range of 15.9 to 72.9 volume percent at one atmosphere total pressure, and outside the range of 18.4–62.0 volume percent at 10 atmospheres total pressure, such explosive ranges being taken from the International Critical Tables, Volume 2, pages 172–190 (McGraw Hill; 1927).

By means of the present invention the need for a separate catalyst plant, viz., for manufacturing Co oleate in which expensive oleic acid is required, and which may be a bottleneck in the oxo process, is avoided. By using a dual demetalling procedure not only is demetalling of crude oxo product achieved efficiently but also active catalyst in the oxo product is extracted and preserved. Furthermore, even though this invention involves recovery and recycling of catalyst, when make-up cobalt is needed this can still be supplied without resort to cobalt soap simply by introducing the required amount of a cobaltous salt of an organic or inorganic acid and processing it along with other similar material. Additionally, the present invention operates on a closed cycle, with no by-products other than water being discharged from the system, so that there are no costs due to environmental protection systems and no adverse effect on the environment. Finally, corrosion concerns associated with any catalyst cycle in which an aqueous cobalt solution is directly injected into the oxo reactors, are eliminated.

The process of this invention can be further illustrated by the following examples wherein parts are by weight unless otherwise indicated. In the Examples, analysis for $Co[Co(CO)_4]_2$ is by EDTA titration of a sample whose total cobalt is oxidized to the $Co^{+2}$ form by use of $H_2O_2$. Concentrations of $Co[Co(CO)_4]_2$ are calculated on the basis of $Co(CO)_4^-$ anion determined by analyzing the CO gas released upon oxidation of the samples with an excess of potassium triiodide. $Co_2(CO)_8$ concentrations are calculated on the basis of elemental cobalt. Concentrations of cobaltous acetate are calculated on the basis of ethylene diamine tetraacetic acid titration. Yields and conversions of $Co_2(CO)_8$ are calculated on the basis of $Co[Co(CO)_4]_2$ consumed.

EXAMPLES 1-2

To illustrate the effect of CO on $Co_2(CO)_8$ yields in the air oxidation of aqueous solutions of $Co[Co(CO)_4]_2$ and cobaltous salts, a 300 cc steel vessel, equipped with a gas inlet valve, is charged under $N_2$ in a series of runs, with an aqueous solution containing $Co[Co(CO)_4]_2$, acetic acid and cobaltous acetate. A selected amount (approximately 50 cc) of 1-dodecene is then charged as organic solvent. The selected gas is then introduced into the vessel, and the 2-phase liquid mixture is kept thoroughly agitated by rocking the vessel, at the indicated conditions of temperature and pressure for the selected period of time. In Example 1, the gas is a mixture of air (150 psig) and CO (240 psig) for a total gas pressure of 390 psig. (It should be noted that this gas composition is in the explosive range, and appropriate precautions should be taken, e.g., use of suitable barracade to protect personnel should be considered, as well as avoiding sources of ignition.) In comparative Example 2, the gas is air (150 psig). Thereafter, the gas is vented, the phases are allowed to settle and are then separated and analyzed. The data thereby obtained are set forth in Table 1 below.

Therefore, the use of CO in the oxidation step is found to result in about a 19% increase in the yield of $Co_2(CO)_8$.

EXAMPLES 3-5

Using an one-gallon stainless steel reaction vessel equipped with a gas inlet valve, stirrer and sample valve provided with a capillary liquid sampling tube, the procedure of Example 1 is repeated, except that the amounts of charged aqueous and organic liquids and the concentrations of $Co[Co(CO)_4]_2$, cobaltous acetate and acetic acid are as indicated. An air/carbon monoxide gas mixture is employed in Examples 3-4. The gas in Example 5 is a mixture of air (150 psig) and $N_2$ (200 psig), the $N_2$ being added to aid in liquid sampling through the capillary tube. At the end of the selected time period, the stirring is stopped and the separated phases are recovered and analyzed. Data obtained are set forth in Table II below. Again, it is found that use of 1850 psig of gaseous CO (in Examples 3 and 4) in combination with 150 psig of air in the oxidation step increased the $Co_2(CO)_8$ yield by about 26 percentage yield points, compared to the use of 150 psig of air alone (Example 5).

Analysis of the separated olefin phase by gas chromatography shows no detectable amounts of olefin oxidation products.

TABLE II

| | Charged Aqueous Solution | | | Charged | Oxidation | | | Product Aqueous Phase | | Product Olefin Phase | |
| --- | --- | --- | --- | --- | --- | --- | --- | --- | --- | --- | --- |
| Example No. | Amount (cc) | Co⁻ (wt %) (1) | Co⁺⁺ (wt %) (2) | Acetic Acid (wt %) | Olefin (1-Dodecene) (cc) | Time (min) | Temp (°C.) | Air/CO Pressure (psig) | Co⁻ (wt %) (1) | Co⁺⁺ (wt %) (2) | $Co_2(CO)_8$ % Yield | % Conv. |
| 3 | 1400 | 0.91 | 1.33 | 2.78 | 1400 | 5 | 25 | 150/1850 | 0 | 1.51 | 80 | 100 |
| 4 | 1400 | 0.91 | 1.33 | 2.78 | 1400 | 5 | 50 | 150/1850 | 0 | 1.50 | 81 | 100 |
| 5 | 1400 | 0.91 | 1.33 | 2.78 | 1400 | 5 | 25 | 150/0 | 0 | 1.74 | 55 | 100 |

Notes:
(1) Cobalt as $Co(CO)_4^-$
(2) Cobalt as $Co^{++}$

EXAMPLES 6-7

The procedure of Examples 3-5 is repeated except that no 1-dodecene is charged prior to oxidation. Rather, the selected aqueous solution, containing the indicated amounts of $Co[Co(CO)_4]_2$, cobaltous acetate and acetic acid, is contacted with the indicated air or air/CO mixture by stirring for the selected time and at the selected temperature and pressure. Thereafter, the gas is vented, and 500 cc of 1-dodecene is charged to the reaction vessel containing the aqueous slurry of $Co_2(CO)_8$. The two-phase mixture is thoroughly agitated for one minute, and the liquid phases are then allowed to settle and are separated and analyzed. The data thereby

TABLE I

| | Charged Aqueous Solution | | | Charged | Oxidation | | | Product Aqueous Phase | | Product Organic Phase | |
| --- | --- | --- | --- | --- | --- | --- | --- | --- | --- | --- | --- |
| Example No. | Amount (Gms) | Co⁻ (wt %) (1) | Co⁺⁺ (wt %) (2) | Acetic Acid (wt %) | Olefin Extractant (cc) | Time (min) | Temp (°C.) | Air/CO Pressure (psig) | Co⁻ (wt %) (1) | Co⁺⁺ (wt %) (2) | $Co_2(CO)_8$ % Yield | % Conv. |
| 1 | 49.6 | 0.52 | 0.44 | 5.73 | 49.3 | 5 | 25 | 150/240 | 0 | 0.62 | 65 | 100 |
| 2* | 51.0 | 0.51 | 0.43 | 5.73 | 50.0 | 5 | 25 | 150/0 | 0 | 0.65 | 57 | 100 |

*Comparative
Notes:
(1) Cobalt as $Co(CO)_4^-$
(2) Cobalt as $Co^{++}$ obtained is set forth in Table III below.

TABLE III

| | Charged Aqueous Solution | | | | Oxidation | | | Charged Olefin | Product Aqueous Phase | | Product Olefin Phase | |
|---|---|---|---|---|---|---|---|---|---|---|---|---|
| | | Co⁻ | Co⁺⁺ | Acetic | | | Air/CO | | Co⁻ | Co⁺⁺ | Co₂(CO)₈ | |
| Run No. | Amount (cc) | (wt %) (1) | (wt %) (2) | Acid (wt %) | Time (min) | Temp (°C.) | Pressure (psig) | (1-dodecene) (cc) | (wt %) (1) | (wt %) (2) | % Yield | % Conv. |
| 6 | 1400 | 0.91 | 1.33 | 2.78 | 5 | 25 | 150/1850 | 500 | 0 | 1.49 | 82 | 100 |
| 7* | 1400 | 0.91 | 1.33 | 2.78 | 5 | 25 | 150/0 | 500 | 0.02 | 1.70 | 58 | 98 |

*Comparative
(1) Cobalt as Co(CO)₄⁻
(2) Cobalt as Co⁺⁺

Examples 3–7 are repeated in a series of runs except that the liquid organic extractant comprises hexenes, octenes, nonenes, toluene, hexane, dodecane and a heavy fraction, having the below-indicated composition (obtained by distillation of alcohol hydroformylation product), and similar results are obtained.

ORGANIC SOLVENT COMPOSITION

About 25 wt. % esters of $C_{10}$ acids and $C_{10}$ alcohols, about 20–25 wt. % $C_{20}$ esters from $C_{10}$ alcohols and about 45–55 wt. % $C_{20}$ alcohols from $C_{10}$ aldehyde aldol condensation and hydrogenation.

It will be obvious that various changes and modifications may be made without departing from the invention and it is intended, therefore, that all matter contained in the foregoing description shall be interpreted as illustrative only and not limitative of the invention.

What is claimed is:

1. A process for forming an olefinic liquid containing dissolved dicobalt octacarbonyl suitable for use as feed to an olefin hydroformylation reaction, which comprises contacting an aqueous solution containing a water-soluble tetracarbonylcobaltate salt in an oxidation zone with a molecular oxygen-containing gas in the presence of a liquid olefinic extractant for dicobalt octacarbonyl to oxidize at least a portion of said tetracarbonylcobaltate to dicobalt octacarbonyl; and recovering said olefinic liquid containing dissolved dicobalt octacarbonyl from said oxidation zone, said recovered liquid being substantially free of oxidation by-products formed in said oxidation zone from any portion of said olefinic extractant.

2. The process according to claim 1 wherein the oxidation in said oxidation zone is conducted in the further presence of carbon monoxide gas charged to said oxidation zone to provide a CO pressure in the range of from about 10 to 4500 psig.

3. The process according to claim 1 or 2 wherein said oxidation is conducted at a temperature within the range of from about 0° to 90° C.

4. A process according to claim 1 or 2 wherein said liquid olefinic extractant is employed in an amount of from about 0.1 to 10 volumes of liquid olefinic extractant per volume of said aqueous solution containing said water-soluble tetracarbonylcobaltate salt.

5. The process according to claim 1 wherein said tetracarbonylcobaltate salt comprises a salt having the formula:

$$M^{+n}[Co(CO)_4^-]_n,$$

wherein "M" is a cation selected from the group consisting of Co, alkali and alkaline earth metal, Fe, Cu, Mo, Ni, Al, $NH_4^+$, $H_3NR^+$, $H_2NR_2^+$, $HNR_3^+$, $NR_4^+$, Zn, and $PR_4^+$, wherein "R" is alkyl of 1 to 20 carbon atoms, aryl of 6 to 18 carbon atoms, alkaryl and aralkyl of 7 to 18 carbon atoms and heterocyclic derivatives of the foregoing aromatic groups.

6. A process according to claim 1 or 5 wherein said liquid olefinic extractant comprises a member selected from the group consisting of olefins containing from 6 to 12 carbon atoms, and aryl-substituted alph-olefins.

7. A process for forming an olefinic liquid containing dissolved dicobalt octacarbonyl suitable for use as feed to an olefin hydroformylation reaction, which comprises contacting an aqueous solution containing cobaltous bis-tetracarbonylcobaltate in an oxidation zone with a molecular oxygen-containing gas in the presence of a liquid olefinic extractant for dicobalt octacarbonyl to oxidize at least a portion of said cobaltous bis-tetracarbonylcobaltate to dicobalt octacarbonyl, said oxidation being affected at a temperature within the range of from about 0° to 90° C.; and recovering said olefinic liquid containing dissolved dicobalt octacarbonyl from said oxidation zone, said recovered liquid being substantially free of olefin oxidation by-products formed in said oxidation zone.

8. The process according to claim 7 wherein CO gas is charged to said oxidation zone to maintain a CO pressure in the range of from about 10 to 4500 psig, and to provide a total pressure, calculated by summation of the partial pressures of CO- and $O_2$-containing gases, within the range of from about 20 to 4500 psig.

9. The process according to claim 8 wherein said carbon monoxide is introduced as syn gas mixtures containing hydrogen and carbon monoxide.

10. An improved process for forming dicobalt octacarbonyl which comprises contacting an aqueous solution containing a water-soluble tetracarbonylcobaltate salt in an oxidation zone with a molecular oxygen-containing gas in the presence of gaseous CO charged thereto, to oxidize at least a portion of said tetracarbonylcobaltate to dicobalt octacarbonyl, the partial pressure of carbon monoxide in said oxidation zone being maintained within the range of from about 10 to 4500 psig and the total pressure provided by carbon monoxide and said oxygen-containing gas being within the range of from about 20 to 4500 psig, whereby improved yields of dicobalt octacarbonyl are obtained; and recovering a liquid phase from said oxidation zone containing said dicobalt octacarbonyl.

11. The process according to claim 10 wherein said recovered liquid phase is contacted with an organic solvent for said dicobalt octacarbonyl to form an organic phase containing the dicobalt octacarbonyl and an aqueous phase substantially free of dicobalt octacarbonyl.

12. The process according to claim 10 wherein said oxidation is further conducted in the presence of an organic solvent for said dicobalt octacarbonyl.

13. The process according to claim 10, 11 or 12 wherein said water-soluble tetracarbonylcobaltate salt comprises a salt of the formula:

$$M^{+n}[Co(CO)_4^-]_n,$$

wherein "M" is a cation selected from the group consisting of Co, alkali, and alkaline earth metal, Fe, Cu, Mo, Ni, Al, Zn, $NH_4^+$, $H_3NR^+$, $H_2NR_2^+$, $HNR_3^+$, $NR_4^+$, and $PR_4^+$, wherein "R" is alkyl of 1 to 20 carbon atoms, aryl of 6 to 18 carbon atoms, alkaryl and aralkyl of 7 to 18 carbon atoms and heterocyclic derivatives of the foregoing aromatic groups.

14. A process for demetalling an oxo product contaminated with cobalt-containing catalyst residues and recovering cobalt carbonyls therefrom which comprises:
   (a) treating the oxo product in a first demetalling zone with a first aqueous solution of a $Co^{++}$ salt of an organic or inorganic acid to extract at least a portion of the cobalt-containing catalyst residues from the oxo product into a first aqueous phase and to form products including said $Co^{++}$ salt and $Co[Co(CO)_4]_2$ therein;
   (b) substantially completing the demetalling of the thus treated oxo product by treatment in a second demetalling zone with an aqueous organic or inorganic acid in the presence of oxygen to form a $Co^{++}$ salt of said acid;
   (c) treating said first aqueous phase with synthesis gas in a high pressure reactor at a pressure in the range of from about 15 psig to about 1500 psig and at a temperature in the range of from about 0° to about 200° C., to form a second aqueous solution containing additional quantities of $Co[Co(CO)_4]_2$;
   (d) contacting said second aqueous solution in an oxidation zone with molecular oxygen at a temperature of from about 0° to 90° C. to form $Co_2(CO)_8$;
   (e) contacting the aqueous effluent of step (d) with an organic solvent to extract said $Co_2(CO)_8$; and
   (f) passing said organic solvent extract to an oxo reaction zone as catalyst.

15. A process according to claim 14 wherein in the oxidation zone the temperature is in the range of from about 10° to about 50° C. and the pressure is in the range of from about 15 to 2000 psig.

16. A process according to claim 14 in which an organic solvent is employed in said oxidation zone and the organic solvent extract is recovered therefrom and passed to the oxo reaction zone as catalyst.

17. A process according to claim 14 in which at least part of the aqueous raffinate from the extraction with the organic solvent in step (e) is passed to the first demetalling zone.

18. A process according to claim 14 in which said $Co^{++}$ salt is cobalt acetate, cobalt formate or mixtures thereof.

19. A process according to claim 14 in which the organic solvent is selected from the group consisting of the feed olefins, hydroformylation product, the heavy oxygenated bottoms fraction from the distillation of oxo alcohols and mixtures thereof.

20. A process according to claim 19 in which the organic solvent is a portion of the feed olefins.

21. A process according to claim 14 in which the extraction with the organic solvent in step (e) is carried out in the presence of carbon monoxide gas at a pressure in the range of about 10 to about 2500 psig, at a temperature of from 0° to about 180° C., and with from about 0.1 to 10 volumes of the organic solvent per volume of said aqueous effluent so contacted.

22. The process of claim 14 wherein step (d) is carried out in the additional presence of carbon monoxide gas.

23. The process of claim 16 wherein said organic solvent comprises at least a portion of the feed olefins to the oxo reaction zone and wherein said oxidation zone additionally contains carbon monoxide gas.

* * * * *